United States Patent
Kunes et al.

(10) Patent No.: US 11,298,164 B2
(45) Date of Patent: Apr. 12, 2022

(54) ANTERIOR TETHER TENSIONER

(71) Applicant: K2M, Inc., Leesburg, VA (US)

(72) Inventors: Brian Kunes, Washington, DC (US); Stacy Hollins, New Castle, VA (US); Laurel Blakemore, Falls Church, VA (US); Brian Hsu, Greenwich (AU); John Ferguson, Auckland (NZ)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 17/091,773

(22) Filed: Nov. 6, 2020

(65) Prior Publication Data

US 2021/0137571 A1 May 13, 2021

Related U.S. Application Data

(60) Provisional application No. 62/932,894, filed on Nov. 8, 2019.

(51) Int. Cl.
*A61B 17/70* (2006.01)
*A61B 17/00* (2006.01)

(52) U.S. Cl.
CPC ...... *A61B 17/7091* (2013.01); *A61B 17/7082* (2013.01); *A61B 2017/00367* (2013.01); *A61B 2017/00407* (2013.01)

(58) Field of Classification Search
CPC ............ A61B 17/7076; A61B 17/7083; A61B 17/7085; A61B 17/7091; A61B 2017/00367; A61B 2017/00407; A61B 17/8869
USPC ....................... 606/86 A, 279, 103, 139, 148
See application file for complete search history.

(56) References Cited

U.S. PATENT DOCUMENTS

| 6,090,111 | A | 7/2000 | Nichols |
| 6,595,565 | B2 | 7/2003 | Whiting et al. |
| 7,278,995 | B2 | 10/2007 | Nichols et al. |
| 7,780,730 | B2 | 8/2010 | Saidi |
| 8,142,842 | B2 | 3/2012 | Sugita et al. |
| 8,313,510 | B2 | 11/2012 | Yuan et al. |

(Continued)

FOREIGN PATENT DOCUMENTS

WO 2016172677 A1 10/2016

OTHER PUBLICATIONS

Extended European Search Report for Application No. 20206137.0, dated Apr. 26, 2021, 6 pages.

*Primary Examiner* — Tessa M Matthews
*Assistant Examiner* — Christina Negrellirodriguez
(74) *Attorney, Agent, or Firm* — Lerner, David, Littenberg, Krumholz & Mentlik, LLP

(57) ABSTRACT

A tether tensioner includes a handle assembly, an elongate member extending distally from the handle assembly, and an engaging portion. The handle assembly includes a stationary member, a trigger pivotably coupled to the stationary member, and a spool rotatably supported on the stationary member. The spool is configured to wrap a tether thereabout. The spool is operatively coupled with the trigger such that pivoting of the trigger relative to the stationary member causes rotation of the spool. The elongate member includes a channel configured to slidably receive a tether therethrough. The engaging portion is configured to receive a head portion of a bone screw such that a tether extends from the head portion disposed in the engaging portion to the spool through the channel of the elongate member.

20 Claims, 9 Drawing Sheets

(56) References Cited

U.S. PATENT DOCUMENTS

| | | |
|---|---|---|
| 8,579,943 B2 | 11/2013 | Nichols et al. |
| 8,808,327 B2 | 8/2014 | Yuan et al. |
| 8,906,062 B2 | 12/2014 | Nichols et al. |
| 9,433,441 B2 | 9/2016 | George et al. |
| 9,675,386 B2 | 6/2017 | Akbarnia et al. |
| 10,034,692 B2 | 7/2018 | Palmer et al. |
| 10,470,803 B2 | 11/2019 | Akbarnia et al. |
| 10,548,644 B2 | 2/2020 | George et al. |
| 10,575,879 B2 | 3/2020 | Palmer et al. |
| 2009/0082776 A1 | 3/2009 | Cresina |
| 2010/0030240 A1 | 2/2010 | Brailovski et al. |
| 2011/0106185 A1 | 5/2011 | Gil et al. |
| 2014/0142638 A1* | 5/2014 | Goodwin ........... A61B 17/8076 606/281 |
| 2014/0257397 A1 | 9/2014 | Akbarnia et al. |
| 2019/0059959 A1 | 2/2019 | Serra et al. |

* cited by examiner

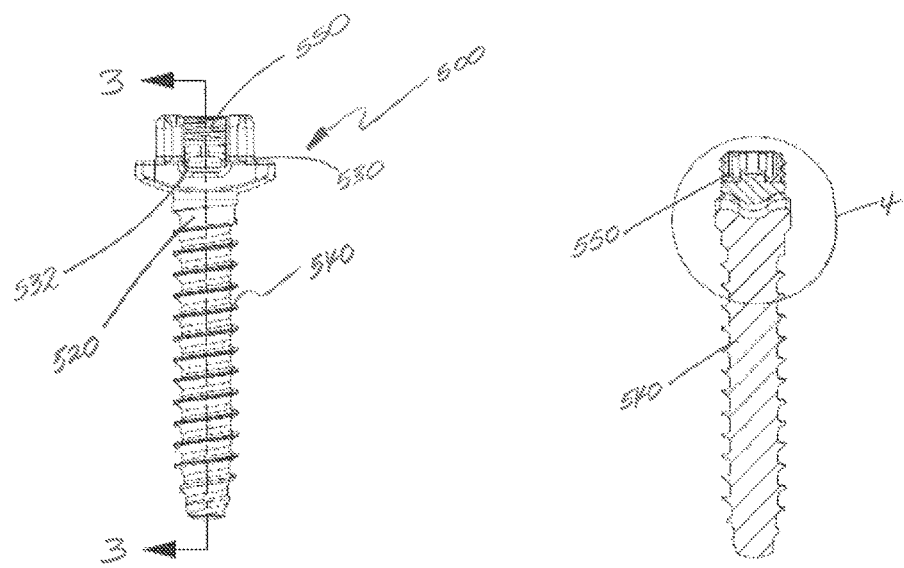
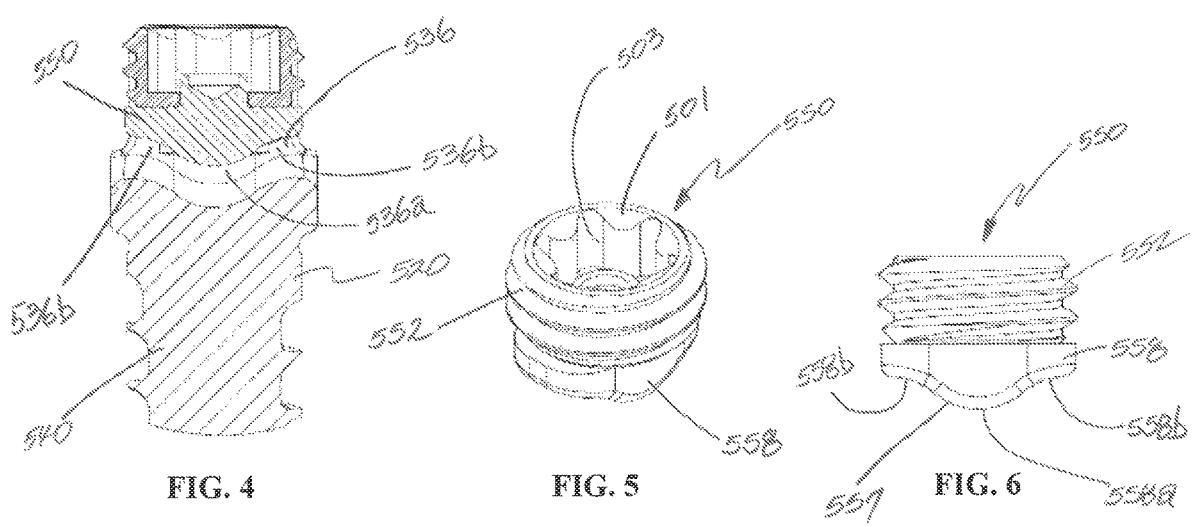
FIG. 2   FIG. 3   FIG. 4   FIG. 5   FIG. 6

ANTERIOR TETHER TENSIONER

CROSS-REFERENCE TO RELATED APPLICATIONS

The present application claims the benefit of the filing date of U.S. Provisional Patent Application No. 62/932,894 filed Nov. 8, 2019, the disclosure of which is hereby incorporated herein by reference.

BACKGROUND

1. Technical Field

The present disclosure relates to surgical devices and, more particularly, to a tether tensioning device.

2. Discussion of Related Art

When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices such as spinal rods are utilized.

In rod-based techniques, one or more spinal rods are attached to the vertebrae at several fixation sites to progressively correct the spinal deformity. The spinal rods are typically pre-curved intraoperatively to a desired adjusted spinal curvature. Wires as well as bone screws can be used to pull individual vertebra toward the spinal rod. The rigidity and permanence of rigid rod-based systems can also hinder or prevent growth of the spine and they generally require fusion of many spine levels, drastically reducing the flexibility of the spine. To help remedy some of these issues, a tether and anchor system can be used to correct curvature of the spine using a number of anchors disposed within the spinal bones that are connected with tethers extending between them. The elasticity of the tethers prevents some of the problems with the rigidity and permanence of the rod-based systems, although the tethers must be tensioned after implantation to achieve the desired force between the anchor to correct the spinal deformities.

Therefore, a continuing need exists for a tether tensioner that can provide adequate tensioning of the tethers to provide spinal correction, while maintaining the safety of the patient.

SUMMARY

In accordance with an embodiment of the present disclosure, a tether tensioner includes a handle assembly, an elongate member extending distally from the handle assembly, and an engaging portion. The handle assembly includes a stationary member, a trigger pivotably coupled to the stationary member, and a spool rotatably supported on the stationary member. The spool is configured to wrap a tether thereabout. The spool is operatively coupled with the trigger such that pivoting of the trigger relative to the stationary member causes rotation of the spool. The elongate member includes a channel configured to slidably receive a tether therethrough. The engaging portion is configured to receive a head portion of a bone screw such that a tether extends from the head portion disposed in the engaging portion to the spool through the channel of the elongate member. In an embodiment, the handle assembly may further include a ratchet wheel operatively coupled with the spool for concomitant rotation therewith. In another embodiment, the trigger may include a rack including teeth to engage teeth of the ratchet wheel. In yet another embodiment, the handle assembly may further include a biasing member to urge the rack towards engagement with the ratchet wheel. In an embodiment, the handle assembly may further include a biasing member to urge the trigger away from the stationary member. In still yet another embodiment, the spool of the handle assembly and the channel of the elongate member may be axially aligned. In an embodiment, the engaging portion may be disposed at a distal portion of the elongate member. In another embodiment, the elongate member may be substantially parallel to the stationary member of the handle assembly. In yet another embodiment, the engaging portion may include a chamber defining an aperture to receive a head portion of a bone screw therethrough. In still yet another embodiment, the elongate member may define a bore dimensioned to receive a tether therethrough. The bore may be in communication with the aperture of the chamber of the engaging portion. In an embodiment, the engaging portion may be positioned with the tether receiving channel of the tensioner aligned with the tether receiving slot of the head of the bone screw. In an embodiment, the chamber may include an inner wall having threads to threadably secure a set screw of a bone screw thereto. In another embodiment, the elongate member may define a groove along a length thereof. The groove may be configured to receive a driver to drive a set screw of a bone screw. In an embodiment, the groove of the elongate member may be aligned with the engagement portion.

In accordance with another embodiment of the present disclosure, a surgical kit includes a tether, a bone anchor including a bone screw and a set screw, and a tether tensioner. The bone screw has a head portion defining a slot dimensioned to receive the tether, and a shank having bone threads and extending from the head portion. The set screw has an anvil portion extending distally from the threaded portion. The anvil portion has a non-planar surface. The tether tensioner includes a handle assembly, an elongate member extending distally form the handle assembly, and an engaging portion. The handle assembly includes a stationary member, a trigger pivotably coupled to the stationary member, and a spool rotatably supported on the stationary member for wrapping the tether thereabout. The spool is operatively coupled with the trigger such that pivoting of the trigger relative to the stationary member causes rotation of the spool. The elongate member includes a channel configured to slidably receive the tether therethrough. The engaging portion is configured to receive the head portion of the bone screw such that the tether extends from the head portion disposed in the engaging portion to the spool through the channel of the elongate member. In an embodiment, the bone screw head portion of the tether tensioner may include an inner wall having threads, and the set screw may include threads. The threads of the bone screw head may be engageable with the threaded portion of the set screw. In another embodiment, the anvil portion of the set screw may include an engaging surface having a convex portion interposed between lateral concave portions. In yet another embodiment, the head portion of the bone screw may have an engaging surface having a concave portion interposed between lateral convex portions. In still another embodiment, the kit may further include a driver configured to drive the set screw. In an embodiment, the elongate member of the tether tensioner may include a groove along a length of the elongate member. The groove may be dimensioned to slidably receive the driver. In another embodiment, the handle assembly of the ratchet tensioner may further include a ratchet wheel operatively coupled with the spool for concomitant rotation therewith. The ratchet wheel may be configured to rotate in a single direction. In another embodiment, the engaging portion of the tether tensioner may include a chamber defining an aperture configured to receive the head portion of the bone screw therethrough. In yet another embodiment, the elongate member of the tether tensioner may define a bore dimensioned to receive the tether therethrough. The bore may be in communication with the aperture of the chamber of the engaging portion.

In accordance with another aspect of the present disclosure, a method of applying tension to a tether includes securing a first end portion of a tether relative to a bone screw; passing a second end portion of the tether through a first slot in a bone screw and through a second slot defined in a distal end of an engaging portion of a tether tensioner; extending the second end portion of the tether through a bore defined in an elongate member of the tether tensioner towards a handle assembly of the tether tensioner; wrapping the second end portion of the tether around a spool of the handle assembly; placing the engaging portion of the tether tensioner over a head portion of the bone screw such that the tether extends through the slot defined in the head portion of the bone screw and into the second slot of the engaging portion; rotating the spool to provide tension in the tether; and securing the tether to the bone screw. In an embodiment, the method may further include manipulating the tether to provide proper tension prior to rotating the spool. In another embodiment, the method may further include partially securing the tether to the second bone screw prior to rotating the spool. In yet another embodiment, securing the first end portion relative to bone may further include securing the first end of the tether to a first bone screw, and looping the tether around an anatomical structure before passing the second end portion of the tether through the tether receiving slots of the bone screw and the engaging portion. In yet another embodiment, the method may further include feeding the second end of the tether through a channel of the elongate member and towards the handle assembly of the tether tensioner. In still yet another embodiment, securing the tether to the second bone screw may include threadably coupling a set screw disposed in the engaging portion to the head portion of the second bone screw to secure the tether therebetween. In yet another embodiment, the set screw may include a first non-planar surface and the first slot of the bone screw includes a second non-planar surface, the method may further comprise tightening the set screw to apply a pressure between the first and second non-planar surfaces to lock the tether disposed therebetween and extending through the first slot.

In accordance with another aspect of the present disclosure, a bone anchor defining a longitudinal axis comprising a head portion having a first opening concentric about the longitudinal axis, a second opening transverse to the longitudinal axis and in communication with the first opening, and a first non-planar surface at a distal end of the first opening, and a set screw receivable in the first opening and having a second non-planar surface at a distal end thereof, the second non-planar surface corresponding to the first non-planar surface, the second opening in communication with the first opening such that a tether passed through the second opening traverses the first opening across the non-planar surface, wherein tightening the set screw applies a pressure between the first and second non-planar surfaces to lock the tether disposed therebetween and extending through the first slot. In other aspects, the bone anchor may further comprise a shank having threads and extending from the head portion. In other aspects, the first opening may include threads and the set screw is threadably receivable in the first opening. In other aspects, a bone anchor system may include the above bone anchor and a tether engaged between the first and second non-planar surfaces.

BRIEF DESCRIPTION OF THE DRAWINGS

Various aspects of the present disclosure are described hereinbelow with reference to the drawings, wherein:

FIG. 2 is a side view of a bone anchor for use with the tether tensioner of FIG. 1;

FIG. 3 is a cross-sectional view of the bone anchor of FIG. 2 taken along section line 3-3 of FIG. 2;

FIG. 4 is an enlarged view of the indicated area of detail of FIG. 3;

FIG. 5 is a perspective view of a set screw of the bone anchor of FIG. 2;

FIG. 6 is a side view of the set screw of FIG. 5;

DETAILED DESCRIPTION

Figure 1:
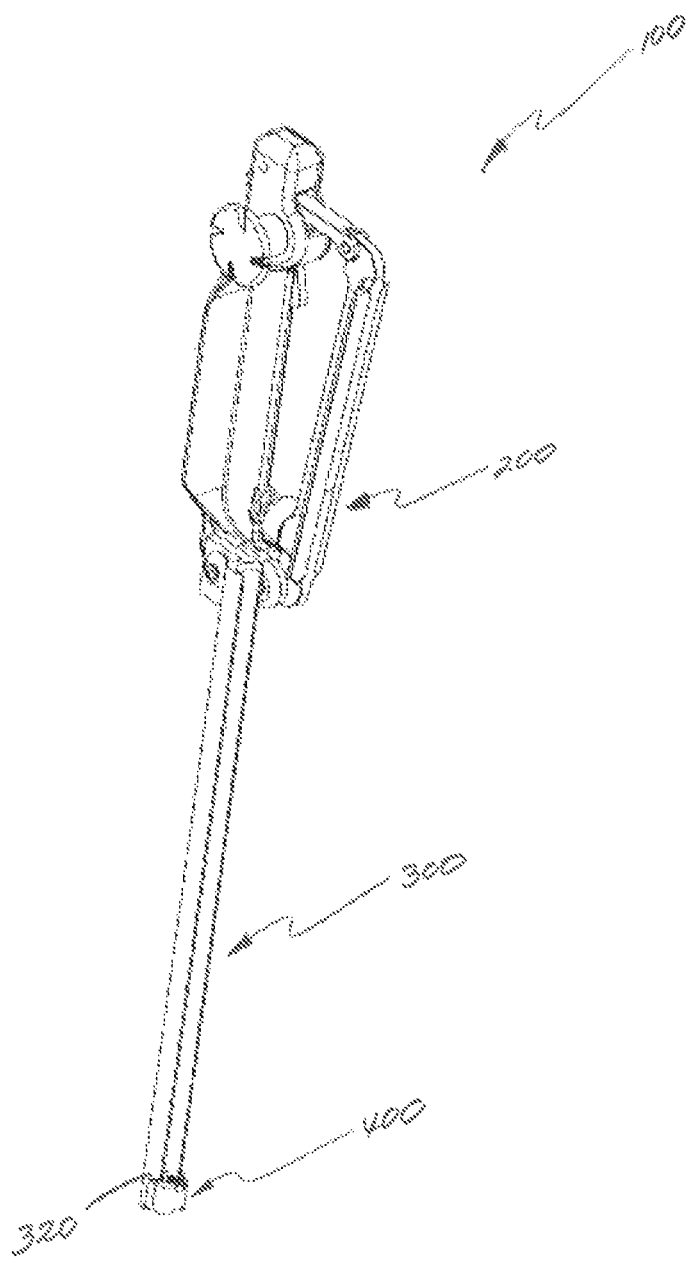
FIG. 1 is a perspective view of a tether tensioner in accordance with an embodiment of the present disclosure.

The presently disclosed tether tensioner will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

With reference to FIG. 1, a tether tensioning device in accordance with an embodiment of the present disclosure is generally shown as a tether tensioner 100. The tether tensioner 100 is configured to provide tensioning of a tether 600 (FIG. 15) extending across one or more bone anchors 500 (FIG. 2) implanted in a bone. The tether tensioner 100 includes a handle assembly 200, an elongate member 300 extending distally from the handle assembly 200, and an engaging portion 400 disposed at a distal portion 320 of the elongate member 300. With reference now to FIGS. 2-6, a bone anchor 500 may be utilized for use with the tether tensioner 100. The bone anchor 500 includes a bone screw 520 and a set screw 550. The bone screw 520 includes a head portion 530 defining a slot 532, and a threaded shaft 540 extending distally from the head portion 530. The slot 532 (FIG. 17) is dimensioned to receive the tether 600 (FIG. 15) and the set screw 550 threadably engaging an inner wall of the head portion 530 to secure the tether 600 to the head portion 530.

Figures 15, 16:
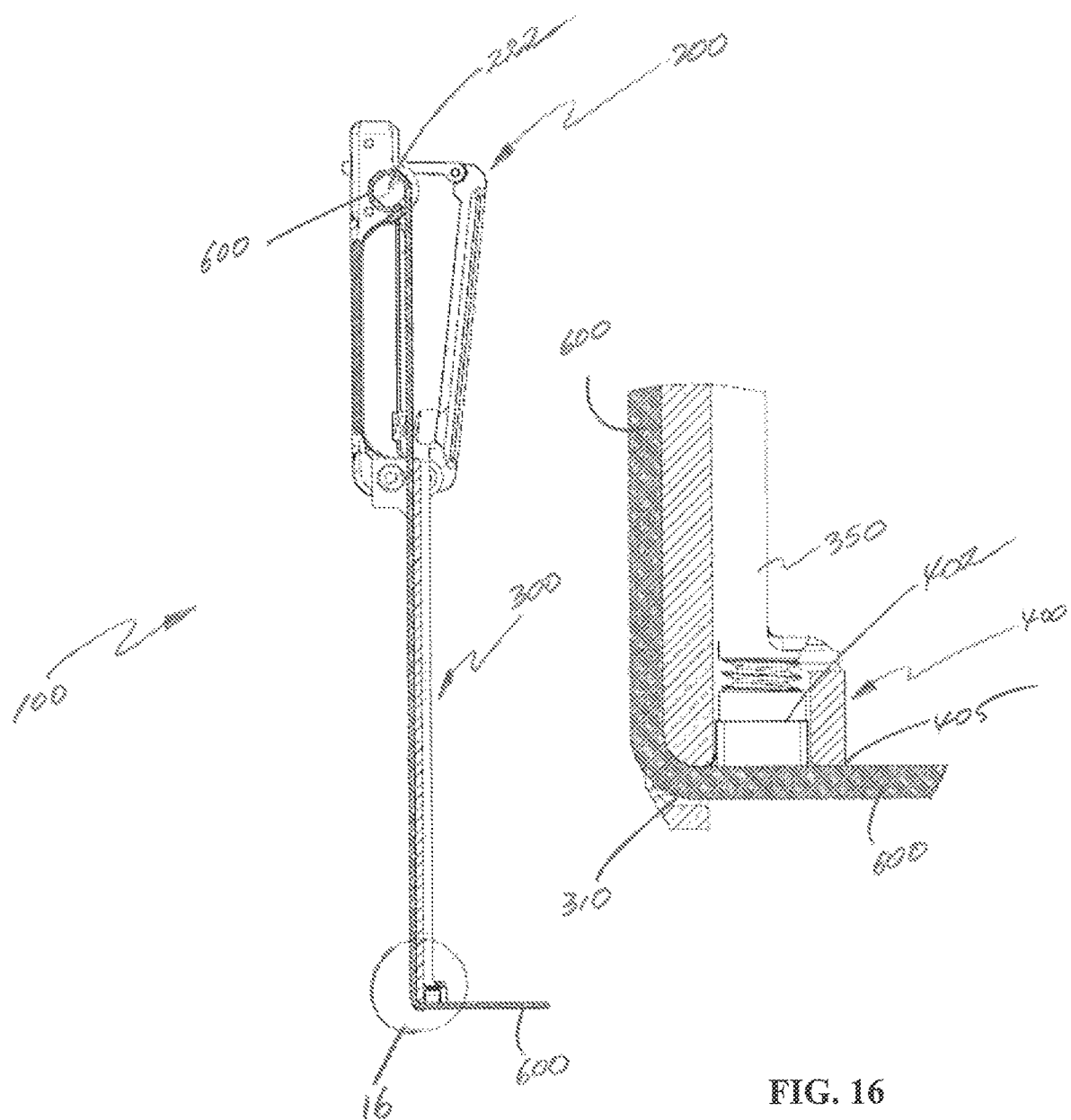
FIG. 15 is a cross-sectional view of the tether tensioner of FIG. 1, illustrating use with a tether.
FIG. 16 is an enlarged view of the indicated area of detail of FIG. 15.

With continued reference to FIGS. 2-6, the head portion 530 of the bone screw 520 preferably includes an engaging surface 536 having a non-planar configuration to engage the tether 600 (FIG. 15). Preferably the non-planar surface configuration is curved, and is received in opposing relation by a corresponding oppositely curved portion of the bone screw to capture and lock a portion of the tether therebetween. The tether 600 may be formed of a material configured to conform to the curvature of the engaging surface 536 when pressed against the engaging surface 536 by the set screw 550. For example, the engaging surface 536 may include a centrally disposed concave portion 536a interposed between laterally opposing convex portions 536b. A curved configuration of the tether locking surfaces are preferable to a flat or angled surface to increase surface contact area, thereby minimizing slipping of the tether, and to avoid sharp edges which might cut into and compromise the integrity of the tether.

With particular reference to FIGS. 5 and 6, the set screw 550 includes a threaded portion 552 configured to be threadably received in the slot 532 (FIG. 2) of the head portion 530 (FIG. 2) of the bone screw 520, and an anvil portion 558 extending distally from the threaded portion 552. In particular, the anvil portion 558 has a distal surface 557 conforming to the curvature of the engaging surface 536 (FIG. 4) of the screw 520. In particular, the distal surface 557 includes a convex portion 558a interposed between lateral concave portions 558b. The convex portion 558a and the lateral concave portions 558b are complementary to the concave portion 536a and the convex portions 536b of the engaging surface 536, respectively. Such a configuration enhances grip pressure of the anvil portion 558 against the tether 600 (FIG. 15) when compared to an anvil portion providing a planar surface contact with the tether 600. The set screw 550 further includes a proximal portion 501 defining a cavity 503 having, e.g., a hex key feature, for non-slip engagement with a driver 700 (FIG. 20) or other instruments to drive the set screw 550 into the head portion 530 (FIG. 2) of the screw 520. It is contemplated that the cavity 503 may have any suitable configuration (e.g., slotted, hexagonal, square, etc.) for engagement with a driving instrumentation. Non-threaded set screws are known and also are contemplated. See for example, U.S. Pat. Nos. 6,090,111, 6,595,565, 7,278,995, 7,780,730, 8,142,842, 8,313,510, 8,579,943, 8,808,327, 8,906,062, the contents of which are hereby incorporated by reference as if repeated herein in their entirety.

Figures 7, 8, 9:
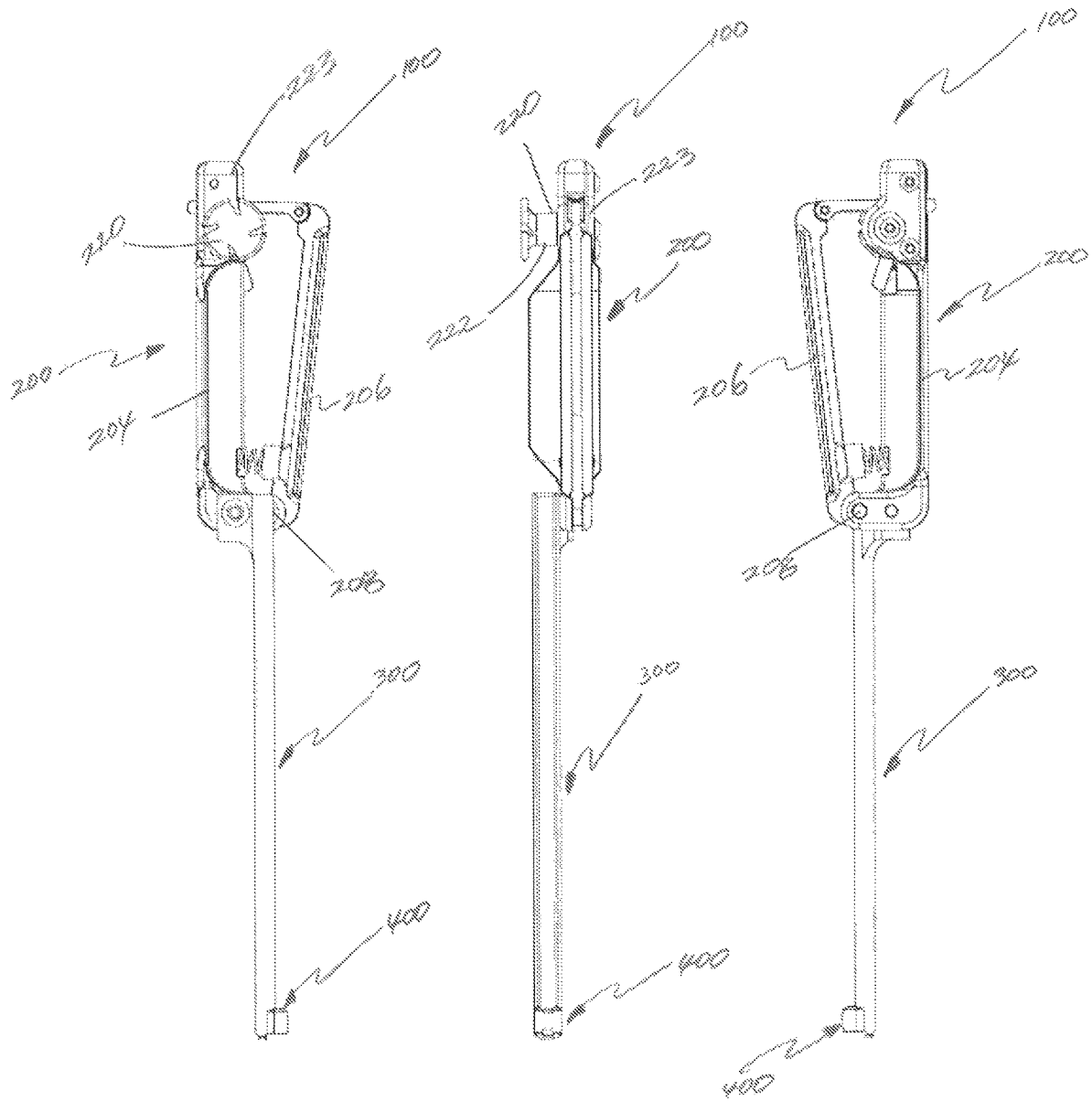
FIG. 7 is a front view of the tether tensioner of FIG. 1.
FIG. 8 is a side view of the tether tensioner of FIG. 1.
FIG. 9 is a rear view of the tether tensioner of FIG. 1.

With reference now to FIGS. 7-9, the handle assembly 200 includes a stationary member 204 and a trigger 206 pivotably coupled with the stationary member 204 about a pivot 208. The trigger 206 is transitionable between a spaced apart position and an approximated position. The stationary member 204 includes a spool assembly 220 configured to wind the tether 600 therearound in order to provide tensioning of the tether 600 (FIG. 15).

Figure 10:
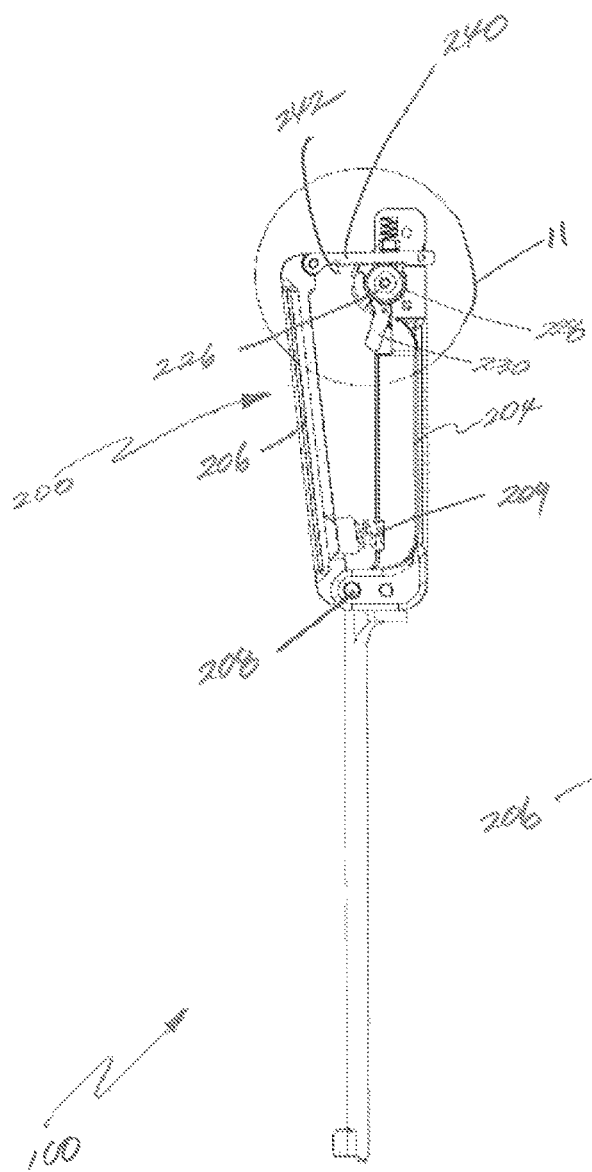
FIG. 10 is a rear view of the tether tensioner of FIG. 1 with a portion of a housing of a handle assembly removed.
Figure 11:
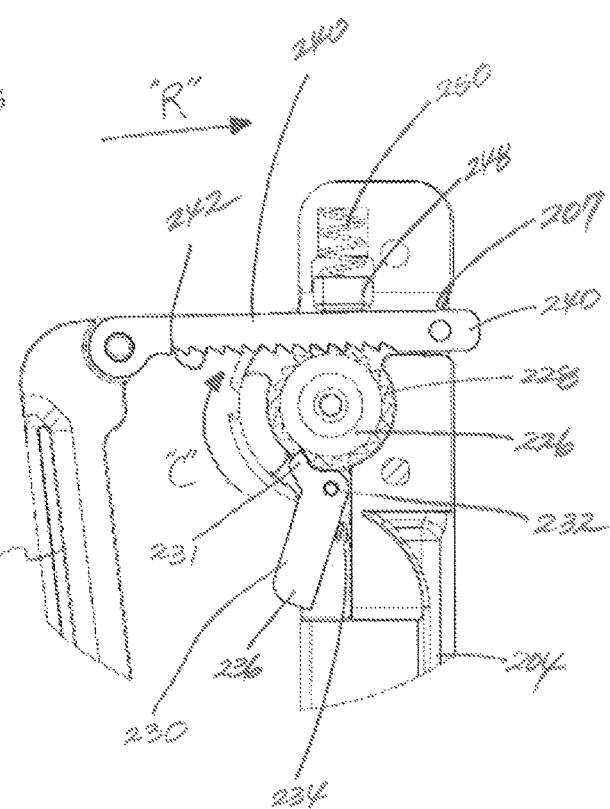
FIG. 11 is an enlarged view of the indicated area of detail of FIG. 10.

With reference to FIGS. 10 and 11, the spool assembly 220 (FIG. 7) includes a housing 223 (FIG. 8) having a ratchet wheel 226 rotatably supported therein, and a spool 222 (FIG. 7) configured to wind the tether 600 therearound. The spool 222 is operatively coupled with the ratchet wheel 226 for concomitant rotation with the ratchet wheel 226. In particular, the spool 222 is disposed exterior to the housing 223. The ratchet wheel 226 includes teeth 228 configured to engage a finger 231 of a pawl 230 that is pivotably supported on the stationary member 204 about a pivot 232. The pawl 230 is biased to urge the finger 231 to engage the teeth 228 of the ratchet wheel 226, by a biasing member 234. In particular, the teeth 228 of the ratchet wheel 226 and the finger 231 are configured to limit rotation of the ratchet wheel 226 to a single direction such as, e.g., clockwise direction "C". Rotation of the ratchet wheel 226 in an opposite direction is inhibited under such a configuration. However, the clinician may press the distal end 236 of the pawl 230 towards the stationary member 204 to disengage the finger 231 from the teeth 228 of the ratchet wheel 226, which, in turn, enables the ratchet wheel 226 to turn in an opposite direction and relieves the tether 600 of tension.

With continued reference to FIGS. 10 and 11, the trigger 206 is pivotably coupled to the stationary member 204 about the pivot 208. The handle assembly 200 further includes a biasing member 209 disposed adjacent the pivot 208 in order to urge the trigger 206 away from the stationary member 204. The trigger 206 further includes a rack 240 having teeth 242 configured to engage the teeth 228 of the ratchet wheel 226. Under such a configuration, the axial displacement of the rack 240 in a direction "R", i.e., linear motion, is converted into rotation of the ratchet wheel 226 in the direction of "C", which, in turn, imparts concomitant rotation to the spool 222 (FIG. 8). The housing 223 (FIG. 8) of the spool assembly 220 further defines a bore 207 dimensioned to receive the rack 240 therethrough. The housing 223 further includes a press 248 coupled to a biasing member 250 such that the press 248 urges the rack 240 to engage the teeth 228 of the ratchet wheel 226.

The handle assembly 200 is dimensioned to fit in a palm of a clinician such that fingers of the clinician wrap around the trigger 206. Under such a configuration, the clinician may squeeze the trigger 206 with the fingers to apply tension to the tether 600 (FIG. 15), as will be described in detail below. The clinician may also use, e.g., an index finger, to squeeze the distal end 236 of the pawl 230 to release tension in the tether 600.

Figures 12, 13, 14:
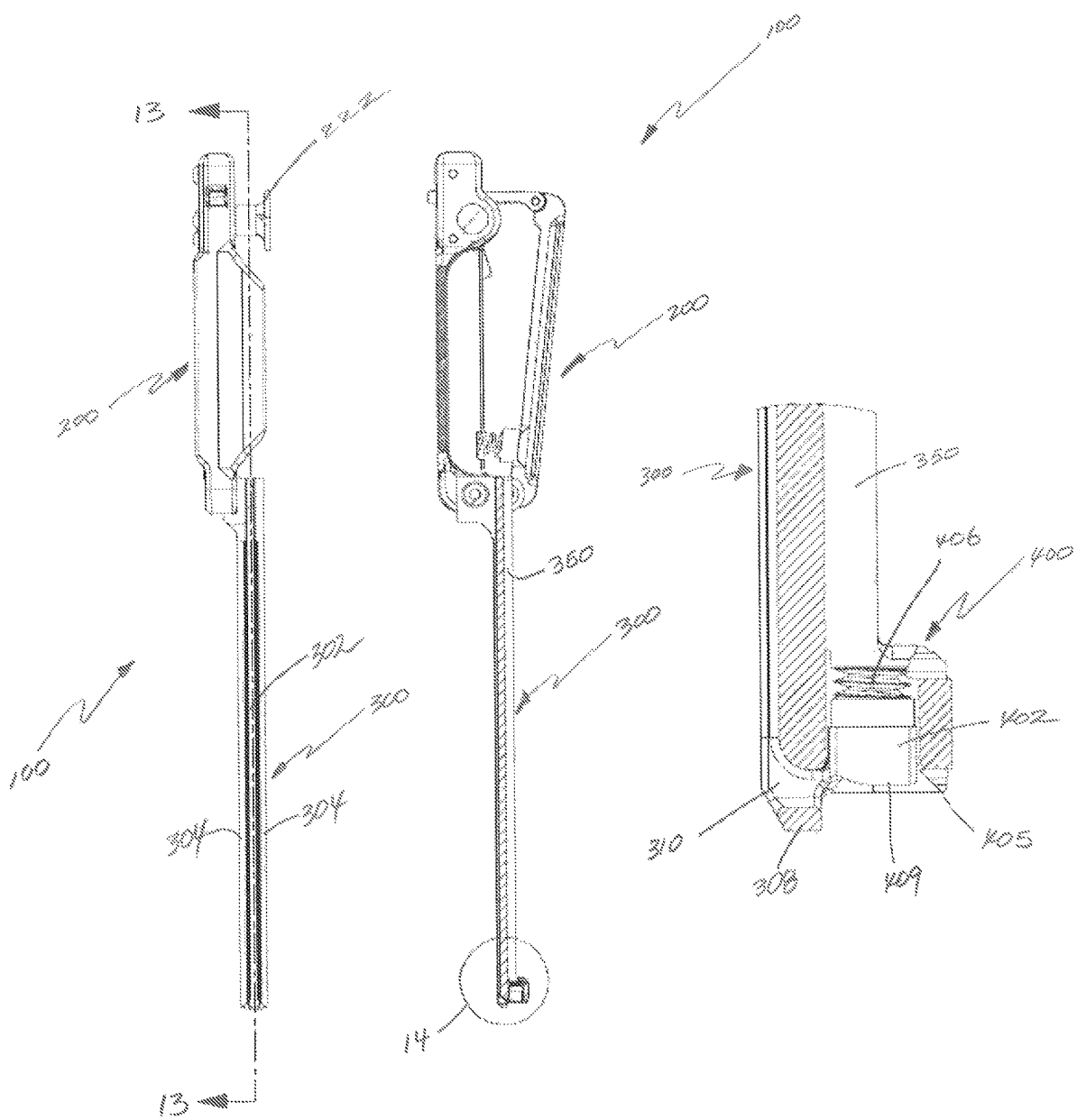
FIG. 12 is another side view of the tether tensioner of FIG. 1.
FIG. 13 is a cross-sectional view of the tether tensioner of FIG. 12 taken along section line 13-13 of FIG. 12.
FIG. 14 is an enlarged view of the indicated area of detail of FIG. 13.

With reference now to FIGS. 12-14, the elongate member 300 extends distally from the handle assembly 200. The elongate member 300 includes a channel 302 extending along the length of the elongate member 300. The channel 302 is aligned with the spool 222 in order to feed the tether 600 (FIG. 15) to the spool 222. In addition, the channel 302 is interposed between guides 304 configured to guide the tether 600 through the channel 302. The elongate member 300 defines an opening 310 at a distal end 308 thereof. The opening 310 is dimensioned to receive the tether 600 therethrough and to direct the tether 600 towards the spool 222 from the engaging portion 400. The elongate member 300 further defines a groove 350 configured to slidably receive a driver 700 (FIG. 20) for driving the set screw 550 into and out of the head portion 530 (FIG. 2) of the screw 520.

With particular reference to FIG. 14, the engaging portion 400 is disposed at the distal portion 320 (FIG. 1) of the elongate member 300. In particular, the engaging portion 400 is positioned to be aligned with the driver 700 (FIG. 20) received through the groove 350 of the elongate member 300. The engaging portion 400 includes a chamber 402 dimensioned to receive the head portion 530 (FIG. 2) of the screw 520. The chamber 402 defines an opening 409 dimensioned to receive the head portion 530 therethrough. An inner wall of the chamber 402 includes threads 406 configured to threadably engage the threaded portion 552 (FIG. 5) of the set screw 550. Under such a configuration, the set screw 550 may be loaded in the engaging portion 400 prior to use.

Figure 17:
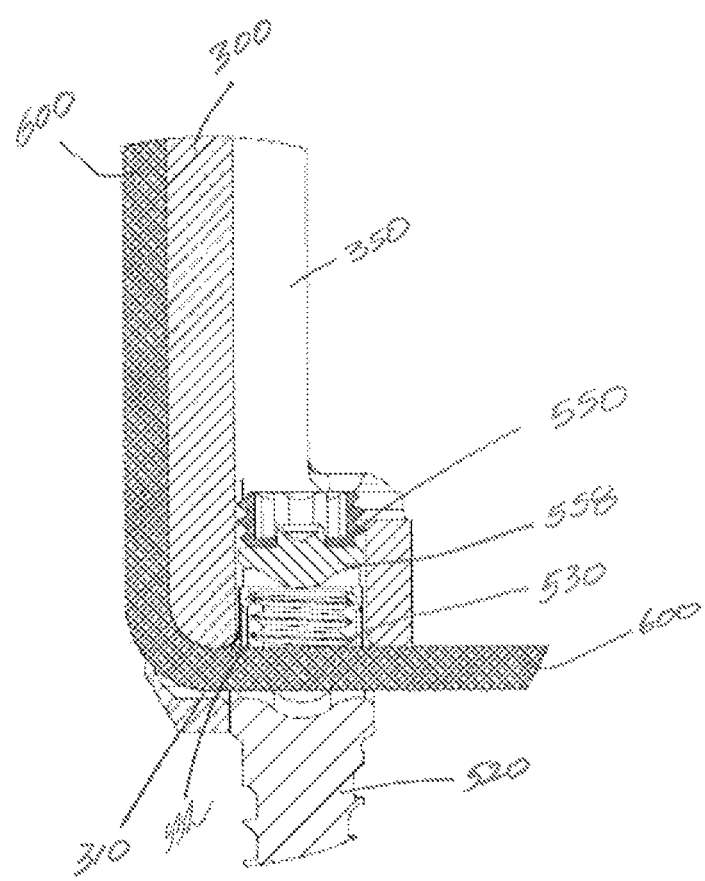
FIG. 17 is a partial cross-sectional view of the tether tensioner of FIG. 1, illustrating use with the bone anchor of FIG. 2.

With reference now to FIGS. 15-17, the tether 600 may extend through a distal portion 405 of the engaging portion 400, i.e., in registration with the opening 409 (FIG. 14). Under such a configuration, when the head portion 530 of the screw 520 is disposed in the chamber 402 of the engaging portion 400, the tether 600 may extend through the slot 532 (FIG. 2) of the head portion 530 and into the opening 310 defined in the elongate member 300.

Figures 18, 19:
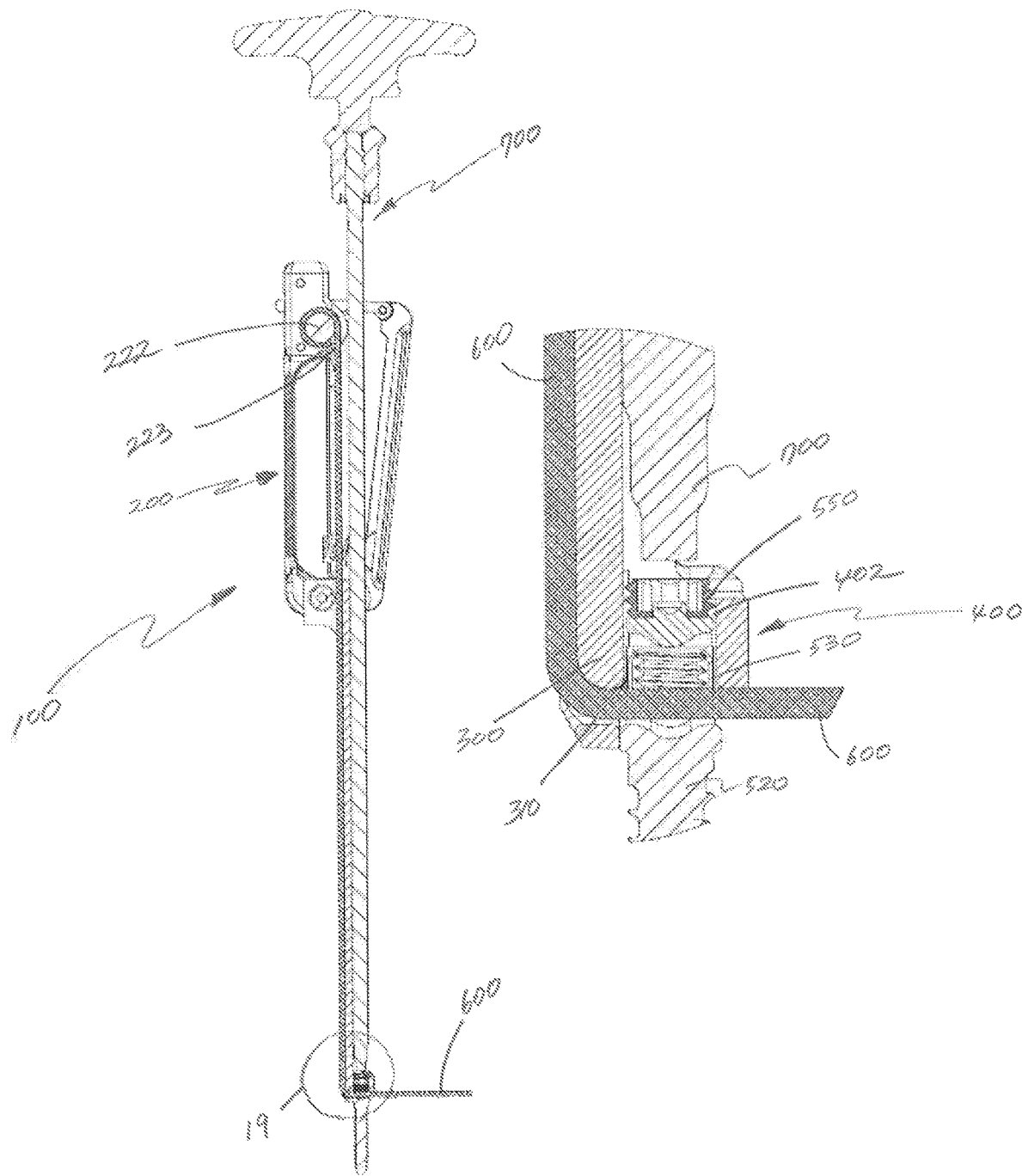
FIG. 18 is a cross-sectional view of the tether tensioner of FIG. 1 and a driver.
FIG. 19 is an enlarged view of the indicated area of detail of FIG. 18.

With reference now to FIGS. 18 and 19, the set screw 550 optionally may be loaded in the chamber 402 of the engaging portion 400 prior to use. After the head portion 530 of the screw 520 is received in the chamber 402 of the engaging portion 400 such that the tether 600 extends through the slot 532 (FIG. 2) of the head portion 530 and the opening 310 of the elongate member 300, the driver 700 may be utilized to drive the set screw 550 into the head portion 530 in order to secure the tether 600 to the bone anchor 500 (FIG. 2). At this time, the tether 600 extending through the opening 310 of the elongate member 300 extends to the handle assembly 200 and is wrapped around the spool 222. The ratchet wheel 226 (FIG. 11) maintains the tether 600 wrapped around the spool 222. Optionally, the spool 222 may be further provided with a clamp or a clip 223 to further secure the tether 600 to the spool 222.

It is envisioned that the tether 600 may be made from various polymers including, e.g., nylon, Dacron®, Ultra-High-Molecular-Weight Polyethylene (UHMWPE), polypropylene, and polyester. It is also contemplated that the tether 600 may include a body, a leader, and a guide wire. The body may include a stiffening wire to increase the stiffness of the body. The stiffening wire may be embedded in the body or may be externally bonded (i.e., bonded on an external surface of the body). The stiffening wire may be bonded along the entire length of the body or only a portion of the length of the body. Reference may be made to U.S. Patent Application Publication No. 2014/0257397, and International Patent Application Publication No. WO 2016/172677, the entire contents of each of which are incorporated herein by reference, for a detailed discussion of the construction and operation of the fastening system.

Figures 20, 21:
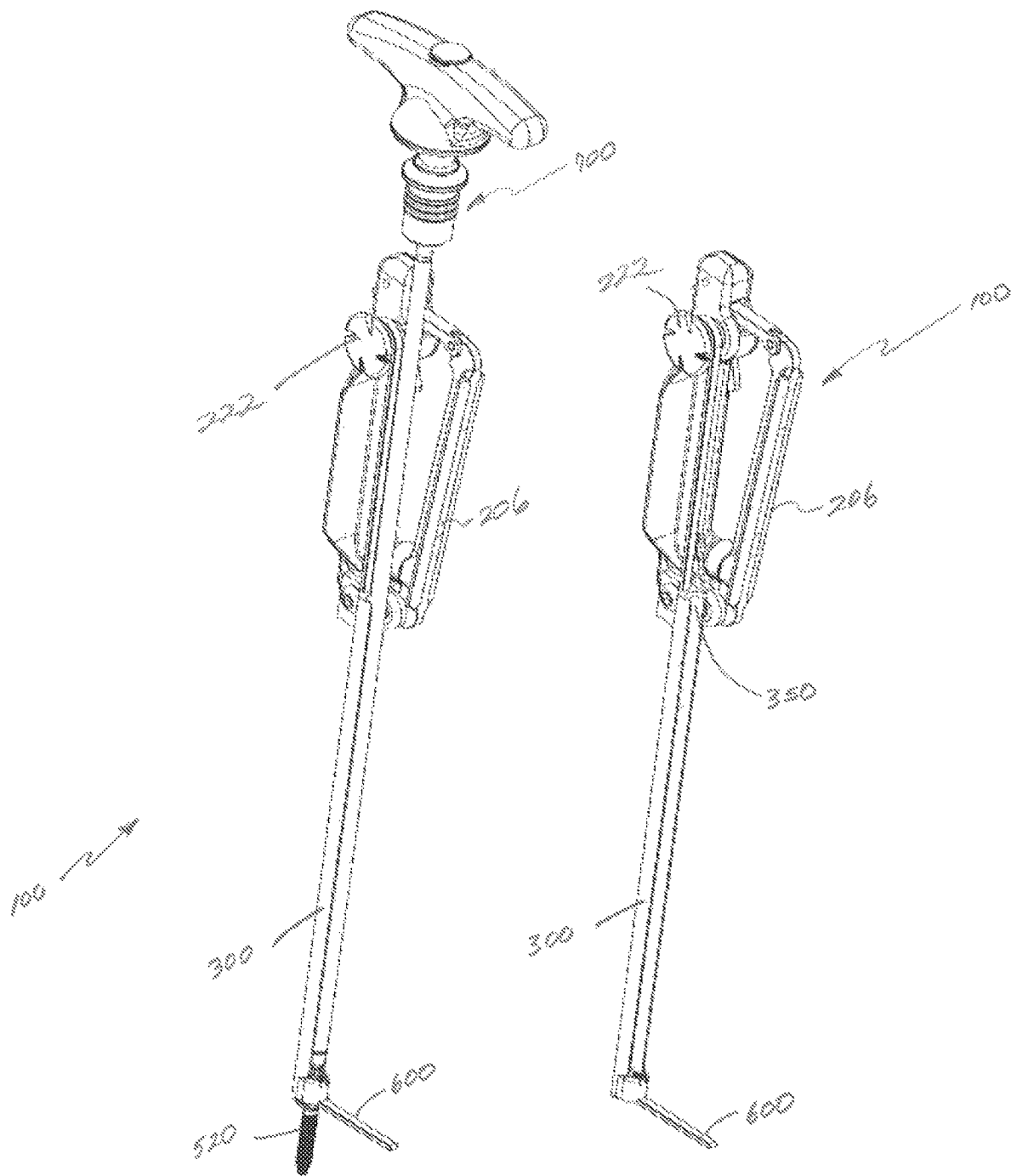
FIG. 20 is a perspective view of the tether tensioner of FIG. 1, illustrating use with a tether.
FIG. 21 is a perspective view of the tether tensioner of FIG. 20, illustrating use with the tether and the bone anchor of FIG. 2.

With reference to FIGS. 20 and 21, in use, two or more screws 520 (FIG. 2) are affixed to anatomical structures of the patient such as, e.g., two or more vertebral bodies. One end of the tether 600 is placed in the slot 532 (FIG. 2) of one of the screws 520 and is secured to the slot 532 by a set screw 550 (FIG. 5). At this time, the tether 600 may be manipulated to provide, e.g., proper alignment or tension, with respect to the vertebral bodies. For example, the tether 600 may form a loop around a vertebral body or be passed around bony structure such as the lamina or spinous process. Thereafter, a free end of the tether 600 is placed adjacent the distal end 405 of the engaging portion 400 and is inserted through opening 409 of the second screw and through opening 310 (FIG. 14) of the elongate member 300. The tether 600 is fed through the channel 302 towards the handle assembly 200. The free end of the tether 600 is then wrapped around the spool 222.

Thus, the tether 600 passes through the mounting portion of the elongate member 300 and through the receiving slot of the second screw, ready to be tensioned. The head portion 530 of the second screw 520 is received in the chamber 402 of the engaging portion 400 such that the tether 600 extends through the slot 532 (FIG. 2) of the head portion 530. At this time, the driver 700 is utilized to at least partially tighten the set screw 550 while still allowing the tether 600 to be tightened. The clinician may squeeze the trigger 206 of the handle assembly 200 in order to remove any slack or to provide tensioning of the tether 600. Once the desired tension in the tether 600 is reached, the driver 700 may be utilized to fully tighten the set screw 550. This process may be repeated for a desired number of bone anchors 500. Alternatively, it is contemplated that the tether and tensioner may be used with a single screw. Thus it will be appreciated that the tether may be secured directly to bone (such as by being passed around bone and through a loop provided one end of the tether) and then passed through slots 409-310 for tensioning, and then secured with set screw 550. Alternatively, it is contemplated that the tether may be passed around bone or other structures, including rods or other portions of a surgical construct, with both ends of the tether passed through slots 409, 310, secured to the tensioning spool, tensioned, and then secured in place with set screw 550. Advantageously, the tether may be loaded to the tensioner outside the body. Thus, the tether may be passed through the bone screw with the bone screw mounted to bone and led out of the incision, where the tether is inserted through the tether engaging slot of the bone screw engaging portion and through the channel to the spool. The tether may be attached to the tensioner at this point or subsequent to positioning the engaging portion onto the bone screw. With the tether fed into the tensioner, the tensioner may be slid down the tether and the engaging portion placed around the bone screw. At this point the slots 409, 310 become aligned to facilitate passage of the tether through the screw into the tensioner. As a further advantage, the set screw and driver may be inserted with the tensioner, and the set screw provisionally engaged with the screw engaging chamber of the bone screw. The tether may be pinned or otherwise secured to the spool, or may simply be passed around the spool multiple times to create a capstan effect to hold the tether to the spool as tension is applied by turning the spool to put the tether under tension. The tether may be secured to the spool with the elongate member of the tensioner inside or outside the body.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A tether tensioner comprising:
   a handle assembly including:
      a stationary member;
      a trigger pivotably coupled to the stationary member; and
      a spool rotatably supported on the stationary member, the spool configured to wrap a tether thereabout, the spool operatively coupled with the trigger such that pivoting of the trigger relative to the stationary member causes rotation of the spool:
   an elongate member extending distally from the handle assembly, the elongate member including a channel configured to slidably receive a tether therethrough; and
   an engaging portion configured to receive a head portion of a bone screw such that a tether extends from the head portion disposed in the engaging portion to the spool through the channel of the elongate member, the tether configured to be locked within the engaging portion by compression between surfaces.

2. The tether tensioner according to claim 1, wherein the handle assembly further includes a ratchet wheel operatively coupled with the spool for concomitant rotation therewith.

3. The tether tensioner according to claim 2, wherein the trigger includes a rack including teeth to engage teeth of the ratchet wheel.

4. The tether tensioner according to claim 3, wherein the handle assembly further includes a biasing member to urge the rack towards engagement with the ratchet wheel.

5. The tether tensioner according to claim 3, wherein the handle assembly further includes a biasing member to urge the trigger away from the stationary member.

6. The tether tensioner according to claim 1, wherein the spool of the handle assembly and the channel of the elongate member are axially aligned.

7. The tether tensioner according to claim 1, wherein the engaging portion is disposed at a distal portion of the elongate member.

8. The tether tensioner according to claim 1, wherein the elongate member is substantially parallel to the stationary member of the handle assembly.

9. The tether tensioner according to claim 1, wherein the engaging portion includes a chamber defining an aperture to receive a head portion of a bone screw therethrough.

10. The tether tensioner according to claim 9, wherein the elongate member defines a bore dimensioned to receive a tether therethrough, the bore in communication with the aperture of the chamber of the engaging portion.

11. The tether tensioner according to claim 9, wherein the engaging portion is positioned with a tether receiving channel of the tensioner aligned with a tether receiving slot of the head of the bone screw.

12. The tether tensioner according to claim 9, wherein the chamber includes an inner wall having threads to threadably secure a set screw of a bone screw thereto.

13. The tether tensioner according to claim 1, wherein the elongate member defines a groove along a length thereof, the groove configured to receive a driver to drive a set screw of a bone screw, wherein the groove of the elongate member is aligned with the engaging portion.

14. A method of applying tension to a tether comprising:
   securing a first end portion of a tether relative to a bone screw; and
   passing a second end portion of the tether through a first slot in a bone screw and through a second slot defined in a distal end of an engaging portion of a tether tensioner;
   extending the second end portion of the tether through a bore defined in an elongate member of the tether tensioner towards a handle assembly of the tether tensioner;
   wrapping the second end portion of the tether around a spool of the handle assembly;
   placing the engaging portion of the tether tensioner over a head portion of the bone screw such that the tether extends through the first slot defined in the head portion of the bone screw and the second slot of the engaging portion;
   rotating the spool to provide tension in the tether; and
   securing the tether to the bone screw.

15. The method according to claim 14, further comprising manipulating the tether to provide proper tension prior to rotating the spool.

16. The method according to claim 14, further comprising partially securing the tether to the bone screw prior to rotating the spool.

17. The method according to claim 16, wherein the step of securing the first end portion relative to the bone screw further comprises securing the first end portion of the tether to the bone screw and looping the tether around an anatomical structure before passing the second end portion of the tether through the first and second slots of the bone screw and the engaging portion.

18. The method according to claim 14, further comprising feeding the second end portion of the tether through a channel of the elongate member and towards the handle assembly of the tether tensioner.

19. The method according to claim 14, wherein securing the tether to the bone screw includes threadably coupling a set screw disposed in the engaging portion to the head portion of the bone screw to secure the tether therebetween.

20. The method of claim 19, where the set screw includes a first non-planar surface and the first slot of the bone screw includes a second non-planar surface, the method further comprising tightening the set screw to apply a pressure between the first and second non-planar surfaces to lock the tether disposed therebetween and extending through the first slot.

* * * * *